US012751612B2

(12) United States Patent
Sinha et al.

(10) Patent No.: US 12,751,612 B2
(45) Date of Patent: Oct. 6, 2026

(54) EYE TRACKING COLOR VISION TESTS

(71) Applicant: Verily Life Sciences LLC, Dallas, TX (US)

(72) Inventors: Supriyo Sinha, Menlo Park, CA (US); Dimitri Azar, Chicago, IL (US); Kirk Gossage, Pacifica, CA (US); Sam Kavusi, Mountain View, CA (US); Prachi Shah, Menlo Park, CA (US); Alexandre Tumlinson, San Leandro, CA (US)

(73) Assignee: Verily Health Inc., Dallas, TX (US)

( * ) Notice: Subject to any disclaimer, the term of this patent is extended or adjusted under 35 U.S.C. 154(b) by 234 days.

(21) Appl. No.: 18/530,062

(22) Filed: Dec. 5, 2023

(65) Prior Publication Data

US 2024/0188818 A1 Jun. 13, 2024

Related U.S. Application Data

(60) Provisional application No. 63/431,223, filed on Dec. 8, 2022.

(51) Int. Cl.
*A61B 3/14* (2006.01)
*A61B 3/00* (2006.01)
(Continued)

(52) U.S. Cl.
CPC ............ *A61B 3/066* (2013.01); *A61B 3/0025* (2013.01); *A61B 3/005* (2013.01); *A61B 3/032* (2013.01); *A61B 3/08* (2013.01); *A61B 3/113* (2013.01); *G02B 27/0093* (2013.01); *G06F 3/013* (2013.01); *H04N 13/324* (2018.05); *H04N 13/344* (2018.05); *H04N 13/383* (2018.05); *G02B 2027/0141* (2013.01)

(58) Field of Classification Search
CPC ........... A61B 3/066; A61B 3/08; A61B 3/113; A61B 3/0025; A61B 3/005; A61B 3/032; G02B 27/0093; G02B 2027/0141; G06F 3/013; H04N 13/383; H04N 13/324; H04N 13/344
USPC .......... 351/209–211, 237, 239; 359/462–477
See application file for complete search history.

(56) References Cited

U.S. PATENT DOCUMENTS 10,281,745 B2 5/2019 Knoll
10,531,795 B1 1/2020 Abou Shousha
(Continued)

FOREIGN PATENT DOCUMENTS

JP 2017504409 2/2017
JP 2021164665 A 10/2021
(Continued)

OTHER PUBLICATIONS

International Search Report and Written Opinion received for PCT Patent Application No. PCT/US23/82653, mailed on May 21, 2024, 22 pages.
(Continued)

*Primary Examiner* — Mahidere S Sahle
(74) *Attorney, Agent, or Firm* — Christensen O'Connor Johnson Kindness PLLC

(57) ABSTRACT

Virtual reality, VR, headset-based and open-display based electronic systems that can be used to perform color vision tests. The systems may improve the sensitivity, consistency, and ease of application of the tests. Other aspects are also described.

16 Claims, 7 Drawing Sheets

(51) Int. Cl.

| | |
|---|---|
| ***A61B 3/02*** | (2006.01) |
| ***A61B 3/032*** | (2006.01) |
| ***A61B 3/06*** | (2006.01) |
| ***A61B 3/08*** | (2006.01) |
| ***A61B 3/113*** | (2006.01) |
| ***G02B 27/00*** | (2006.01) |
| ***G06F 3/01*** | (2006.01) |
| ***H04N 13/324*** | (2018.01) |
| ***H04N 13/344*** | (2018.01) |
| ***H04N 13/383*** | (2018.01) |
| *G02B 27/01* | (2006.01) |

(56) References Cited

U.S. PATENT DOCUMENTS

| | | | | |
|---|---|---|---|---|
| 11,612,316 B2 | 3/2023 | Zidan et al. | | |
| 11,733,542 B2 | 8/2023 | Macnamara et al. | | |
| 2014/0198382 A1* | 7/2014 | Chen | G02C 11/10 | 359/464 |
| 2020/0073143 A1 | 3/2020 | Macnamara et al. | | |
| 2020/0397288 A1 | 12/2020 | Zidan et al. | | |
| 2021/0076930 A1 | 3/2021 | Blaha et al. | | |
| 2021/0378504 A1 | 12/2021 | Monti | | |
| 2022/0322930 A1* | 10/2022 | Fateh | A61B 3/16 | |

FOREIGN PATENT DOCUMENTS

| | | | |
|---|---|---|---|
| KR | 1020220041959 A | 4/2022 | |
| WO | WO-2022066744 A1 * | 3/2022 | A61B 3/10 |
| WO | 2022/082171 A1 | 4/2022 | |
| WO | 2023/250163 A2 | 12/2023 | |

OTHER PUBLICATIONS

Voraphani, Natthapongs; Color vision screening using eye movements; Retrospective Theses and Dissertations; 15728; 2007; https://lib.dr.iastate.edu/rtd/15728; 130 pages.

"Procedures for Testing Color Vision: Report of Working Group 41;" Committee on Vision; Assembly of Behavioral and Social Sciences; National Research Council; National Academy Press; Washington, D.C.; 1981; http://www.nap.edu/catalog/746.html; 129 pages.

Gomez, Argenis Ramirez, et al.; "Gaze+Hold: Eyes-only Direct Manipulation with Continuous Gaze Modulated by Closure of One Eye;" In 2021 Symposium on Eye Tracking Research and Applications (ETRA '21 Full Papers); May 25-27, 2021; Virtual Event, Germany; ACM, New York, NY, USA; https://doi.org/10.1145/3448017.3457381; 12 pages.

Taore, Aryaman, et al.; "Diagnosis of colour vision deficits using eye movements;" Scientific Reports; 2022; www.nature.com/scientificreports/; 12:7734; https://doi.org/10.1038/s41598-022-11152-5; 14 pages.

Cavanagh, Patrick, et al.; "The Contribution Of Color To Motion In Normal And Color-Deficient Observers;" Vision Res. vol. 31, No. 12; 1991; pp. 2109-2148.

Turpin, Andrew, et al.; "Development of Efficient Threshold Strategies for Frequency Doubling Technology Perimetry Using Computer Simulation;" Investigative Ophthalmology & Visual Science; Feb. 2002; vol. 43, No. 2; pp. 322-331.

"Types of Color Blindness;" National Eye Institute; https://www.nei.nih.gov/learn-about-eye-health/eye-conditions-and-diseases/color-blindness/types-color-blindness; Dec. 7, 2022; 2 pages.

"Color Perception;" Welcome to the World of Colors; https://www3.cs.stonybrook.edu/~lori/classes/ColorPerception/categories.html#:~:text=Precisely%2C HUE is the name, or purity of a color; Oct. 18, 2022; 1 page.

Japanese Office Action mailed Apr. 13, 2026, in corresponding Japanese Patent Application No. 2025-523026.

* cited by examiner

EYE TRACKING COLOR VISION TESTS

CROSS-REFERENCE TO RELATED APPLICATION

This nonprovisional patent application claims the benefit of the earlier filing date of U.S. Provisional Application No. 63/431,223 filed 8 Dec. 2022.

FIELD

An aspect of the disclosure here relates to portable head worn equipment that can be used for performing hands-free color vision testing of the wearer's eyes. Other aspects include eye tracking color vision testing using motion stimuli.

BACKGROUND

Traditionally, color vision is assessed using pseudo-isochromatic plates, PIPs, which hide patterns in images consisting of many single-color bubbles that vary from bubble to bubble within a range of size, hue, and intensity. The patterned symbols, created from groups of neighboring bubbles with a different hue range than the background bubbles, are visible to an individual with normal color vision but are hidden from an individual with impaired color vision or sensitivity.

Traditional PIP tests present a static image on a printed plate and the individual is asked to identify the image that they are observing, usually by a verbal response. Electronic versions of these tests exist where the testing strategy is similar in that the individual is asked to enter a number or character that they see or select from a set of options.

SUMMARY

One aspect of the disclosure here is a stereoscopic system that can be used to perform a color vision test or examination (exam) in a repeatable manner that not only quantifies the tested individual's degree of color blindness but also can show its progression over time. In the case where a virtual reality, VR, headset is used, these systems may improve consistency and ease of conducting the color vision test in various ambient light environments, in a more efficient (less time consuming) manner. The results of the test may then be used by, for example, an eye care professional to diagnose a health problem with the person that might call for additional testing or a recommended treatment. Other aspects are directed to eye tracking color vision testing using motion stimuli.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have advantages that are not recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
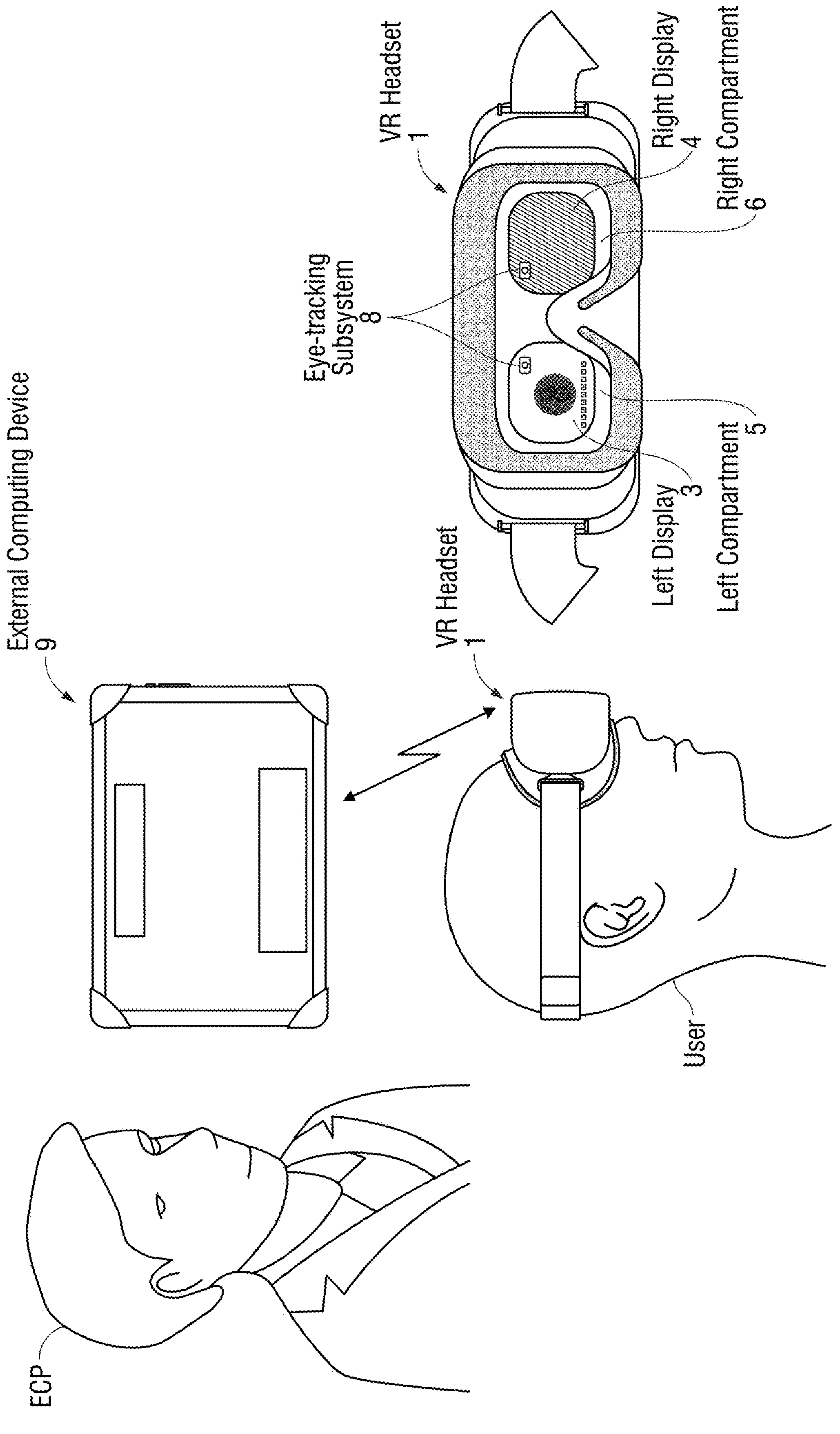
FIG. 1 is a diagram of an example virtual reality, VR, headset-based system for color vision testing.

FIG. 1 is a diagram of an example virtual reality, VR, headset-based system that can be used for color vision testing. The system is an example of a stereoscopic system, where some of the aspects described below are also applicable in other stereoscopic systems such those that use a lenticular array. The system in FIG. 1 is composed of a VR headset 1 which 1 is fitted over the eyes of a user (observer) as shown. It has a wired or wireless communication network interface for communicating data with an external computing device 9, e.g., a tablet computer, a laptop computer, etc. A human operator, such as an eye care professional, ECP, may interact briefly with software that is being executed by one or more microelectronic data processors (generically, "a processor") of the system to conduct the color vision test. Once launched or initialized the software may conduct the test automatically (without input from the operator) by controlling the various electronic and optical components of the VR headset 1. The software may have components that are executed by a processor that is in the VR headset 1, and it may have components that are executed by a processor which is part of the external computing device 9. Some of these software components may be executed either in the VR headset 1 or in the external computing device 9. The software may interact with the operator through a graphical user interface component that uses a touchscreen of the external computing device 9 for presenting results of the color vision test.

The VR headset 1 may have a form factor like goggles, as shown, that blocks all ambient lighting outside of the VR headset 1 so as to create a light controlled environment around the user's eyes (that is independent of the ambient lighting outside of the VR headset 1.) The VR headset 1 may be composed of a left visible light display 3 to which a left compartment 5 is coupled that fits over the left eye of the user, and a right visible light display 4 to which a right compartment 6 is coupled that fits over the right eye of the user. The left and right compartments are configured, e.g., shaped and being opaque, so that the user cannot see the right display 4 using only their left eye, and the user cannot see the left display 3 using only their right eye (once the VR headset 1 has been fitted over the user's eyes.) Also, the left and right displays need not be separate display screens, as they could instead be the left and right halves of a single display screen. The displays may be implemented using technology that provides sufficient display resolution or pixel density, e.g., liquid crystal display technology, organic light emitting diode technology, etc. Although not shown, there may also be an eyecup over each of the left and right displays that includes optics (e.g., a lens) serving to give the user the illusion that an object they see in the display (in this example a pine tree, which may be displayed in 2D or in 3D) is at a greater distance than the actual distance from their eye to the display, thereby enabling more comfortable viewing. The VR headset 1 might also incorporate trial lenses or some other adjustable refractive optical system to accommodate patients with different refractive errors.

The VR headset 1 also has a non-visible light-based eye tracking subsystem 8, e.g., an infrared pupil tracking subsystem, whose output eye tracking data can be interpreted by the processor for independently tracking the positions of the left and right eyes, and for detecting blinks and pupil size or diameter of each eye, in a way that is invisible to the user.

Figure 2A:
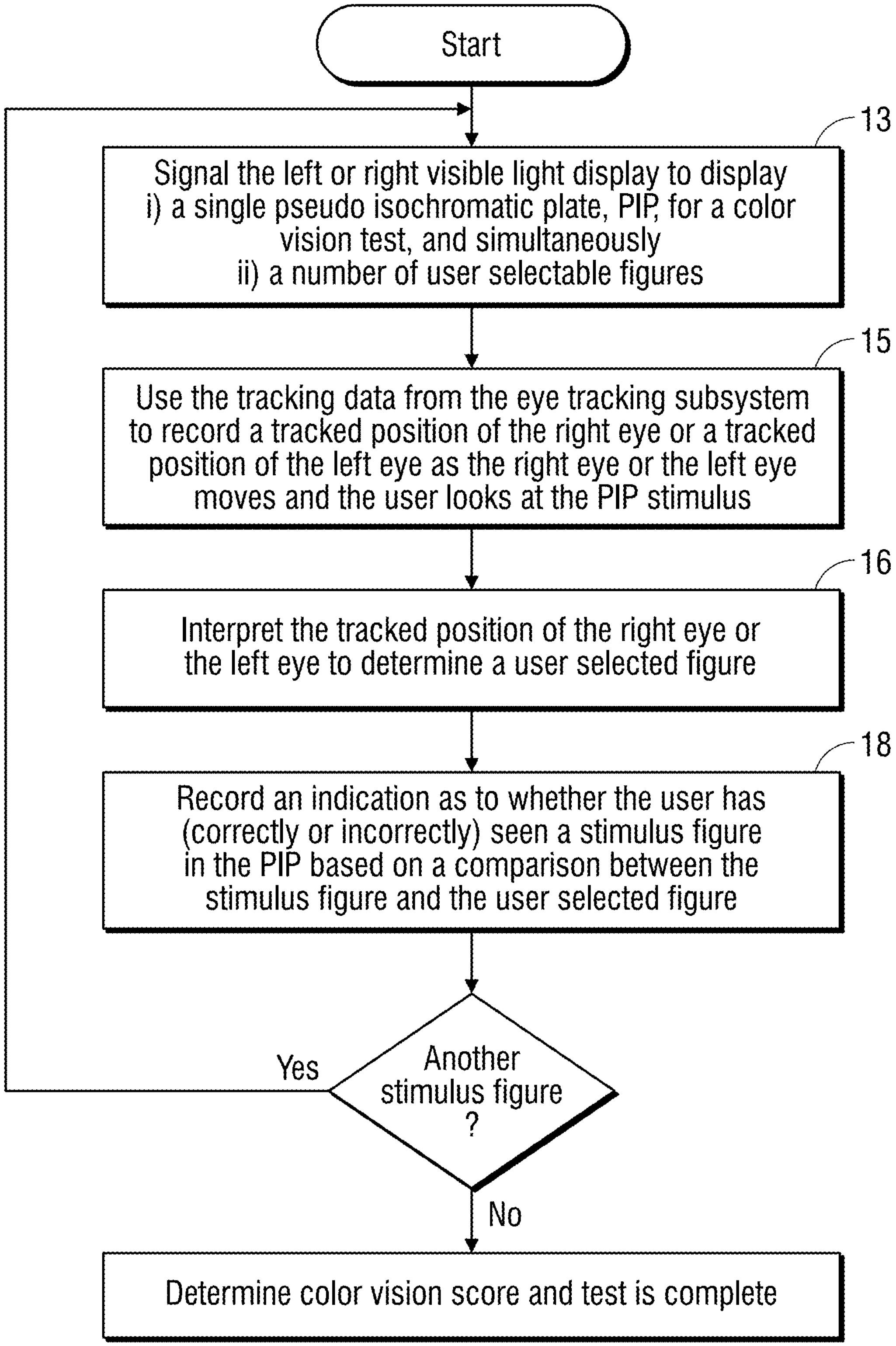
FIG. 2A is a flow diagram of an example method for color vision testing.

The system has a processor, e.g., one or more microelectronic processors that are part of the external computing device 9, one or more that are within the housing of the VR headset 1, or a combination of processors in those devices that are communicating with each other through a communication network interface. The processor is configured by software, or instructions stored in a machine readable medium such as solid state memory, to conduct a color vision test, when the headset has been fitted over the user's eyes. To do so, the processor signals the left or right visible light display to display a stimulus for the color vision test that the user sees using their left or right eye, respectively. The processor may be configured to signal a further display, for example the display screen of the external computing device 9, to display progress of or the results of test. The test may proceed as follows, referring now to FIG. 2A.

The user is instructed, for example directly by an eye care professional, ECP, in-person or via previously recorded instructions that are played back through a speaker, to fit the VR headset 1 over their eyes and look for a stimulus that will be displayed by the left visible light display or the right visible light display. As shown in the flow diagram of FIG. 2A, the processor may then begin the test with operation 13 by signaling the left or right visible light display to display i) a single pseudo isochromatic plate, PIP, for a color vision test, e.g., an Ishihara plate, and simultaneously ii) a number of user selectable figures—see FIG. 2B which shows an example of nine user selectable figures as being the numbers 1-9, respectively. A user selectable figure may be a number, a letter, or another symbol that is hidden in the PIP, wherein FIG. 2B the figure is the number "8". While the PIP is being shown, the processor uses the tracking data from the eye tracking subsystem 8 to record a tracked position of the right eye or a tracked position of the left eye (operation 15) as the right eye or the left eye moves and the user looks at the PIP stimulus. The processor interprets the tracked position of the right eye or the left eye to determine a user selected figure (operation 16), which has been selected by the user from amongst the several user selectable figures—a form of multiple choice question. The processor then records an indication as to whether the user has seen a stimulus figure in the PIP (operation 18), based on a comparison between the stimulus figure and the user selected figure—as a correct or incorrect answer to the question. The processor then repeats operations 13-18 one or more times, wherein each time the PIP contains a different stimulus figure. This results in several indications being recorded, as to whether the user has (correctly or incorrectly) seen the various stimulus figures. The processor may thus complete the test on the user without receiving manual or verbal input from the user on whether the user has seen the stimulus figures.

In one aspect, the processor in operation 16 is configured to interpret the tracking data of the eye tracking subsystem to detect a blink by the user, while the PIP plate is being displayed in operation 13. It then determines the user selected figure based on the detected blink occurring while the user is gazing at a particular user selected figure. In another aspect, the processor determines the user selected figure based on merely detecting that the user's gaze has remain fixed on a particular user selected figure for some time.

In another aspect, the processor quantifies hesitancy by the user, in terms of the time interval between the PIP appearing and the user selecting one of the figures. The hesitancy can be used the processor to provide more information than just binary correct or incorrect selection of the figure. For example, if a user correctly selects some PIPs quickly as compared to others, then that could provide additional information on the color sensitivity of the user's eye.

In one aspect, the processor performs operations 13-18 several times wherein each time the display of the PIP in operation 13 alternates between the left visible light display and the right visible light display, and in operation 18 the indication as to whether the user has seen the stimulus figure in the PIP refers to only the left eye or only the right eye, respectively.

Figure 2B:
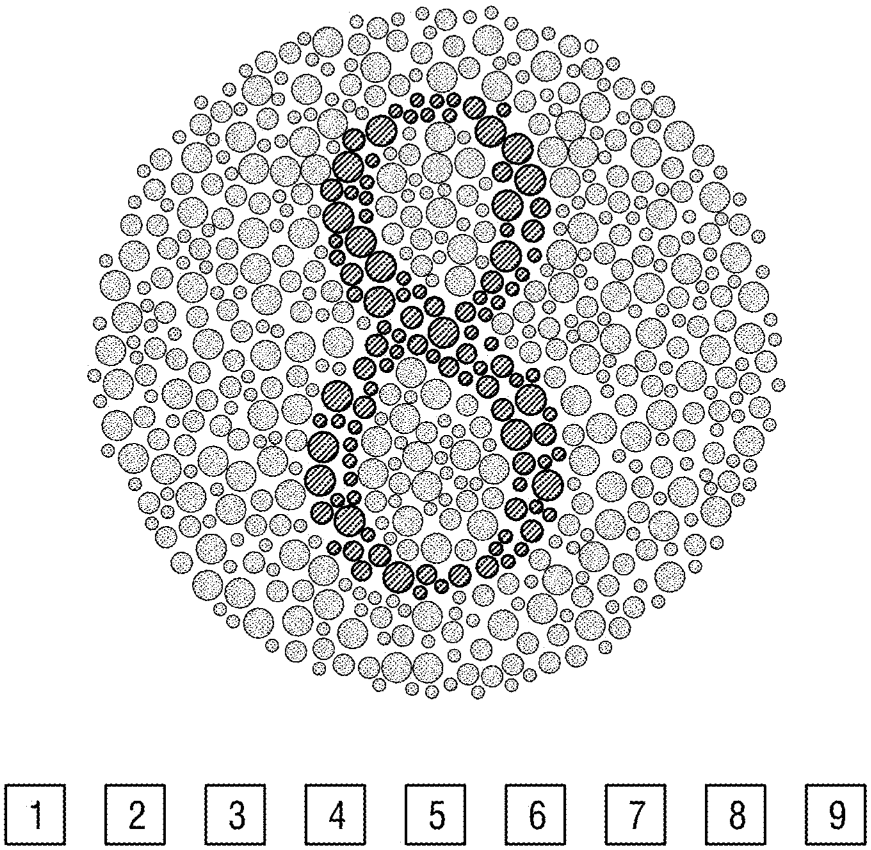
FIG. 2B shows an example PIP having a figure that is hidden amongst a background of colored bubbles, and a number of user selectable figures, being displayed to an eye of the user.

In the example of FIG. 2B, the nine user selectable figures are not only visible (where each number is visible to the user) but they are arranged in a straight line below the plate. As another example of the hands-free color vision test, the system could display the user selectable figures in a clock dial arrangement, and the single plate having a single hidden number in it, selected from 1-12, is displayed for example in the middle of a clock face (with or without moving hands.) In such a clock dial/clock face version, the user selectable figures could be replaced with generic marks (e.g., at the 12, 3, 6 and 9 positions only of the clock dial) without any numbers in the clock dial. In both instances, the user would be instructed to try to recognize the hidden number that is being displayed on the plate and then look towards or in the direction of the clock dial, where the hidden number would be located as expected on a clock. For example, if the user recognizes the hidden number as being 6, then they would look vertically down, or if they recognize the hidden number as being 3 then they would look horizontally to the right, etc. The numbers may be added to all twelve positions of the clock dial.

Figure 3:
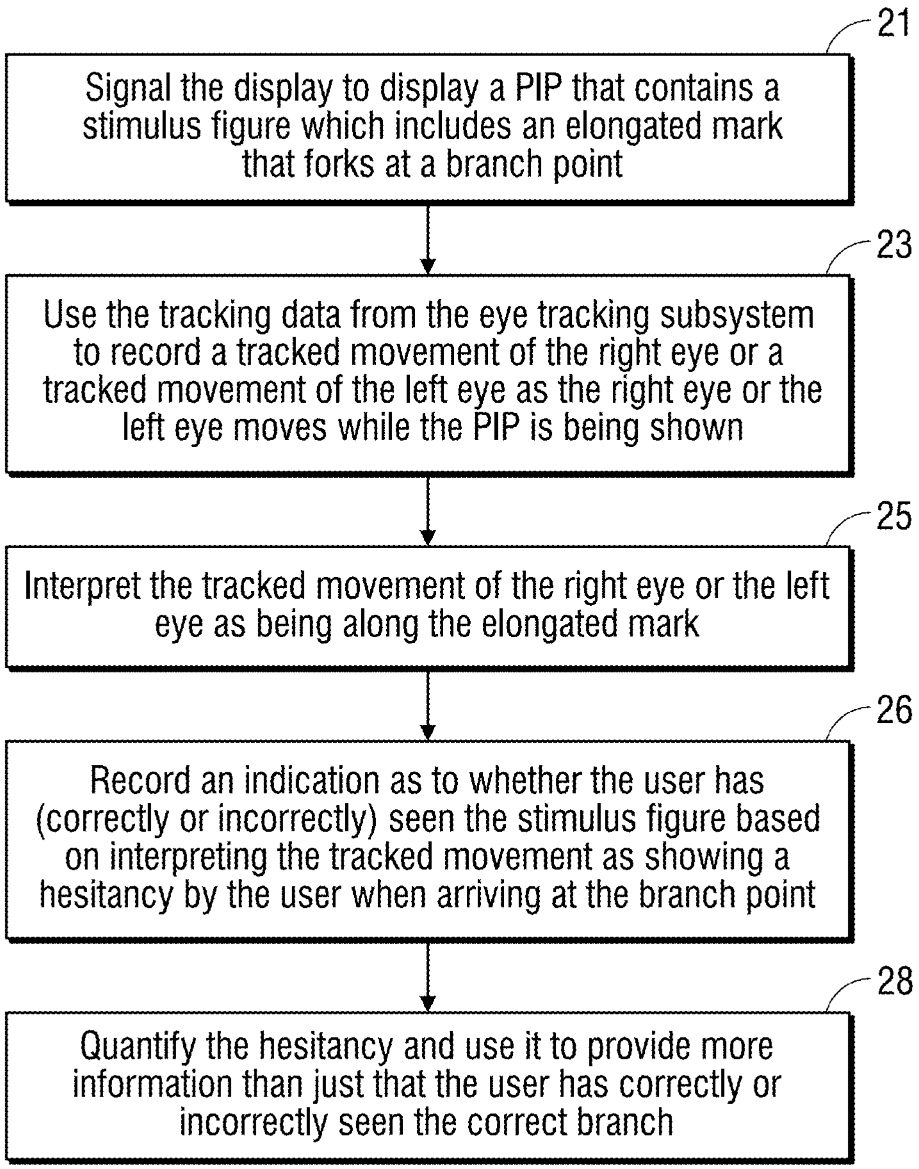
FIG. 3 is a flow diagram of another example method for color vision testing.

In yet another aspect, referring now to the flow diagram in FIG. 3, beginning with operation 21, the color vision test is conducted by the processor signaling the display to display a PIP that contains a hidden stimulus figure which includes an elongated mark that forks at a branch point e.g., as in the letter "Y". As above, the processor uses the tracking data from the eye tracking subsystem 8 to record a tracked movement of the right eye or a tracked movement of the left eye (in operation 23) as the right eye or the left eye moves while this PIP is being shown. It then interprets the tracked movement of the right eye or the left eye as being upward along the elongated mark (in operation 25.) For example, the user may be tracing over the stem of the letter "Y." The processor then in operation 26 records an indication as to whether the user has seen the stimulus figure based on interpreting the tracked movement as showing a hesitancy by the user when arriving at the branch point or fork of the letter "Y". The processor may also quantify the hesitancy here, in terms of the time interval between arriving at the branch point and then resuming tracing along one of the branches. The processor can use this to provide more information than just that the user has correctly or incorrectly seen the branch.

Figure 4:
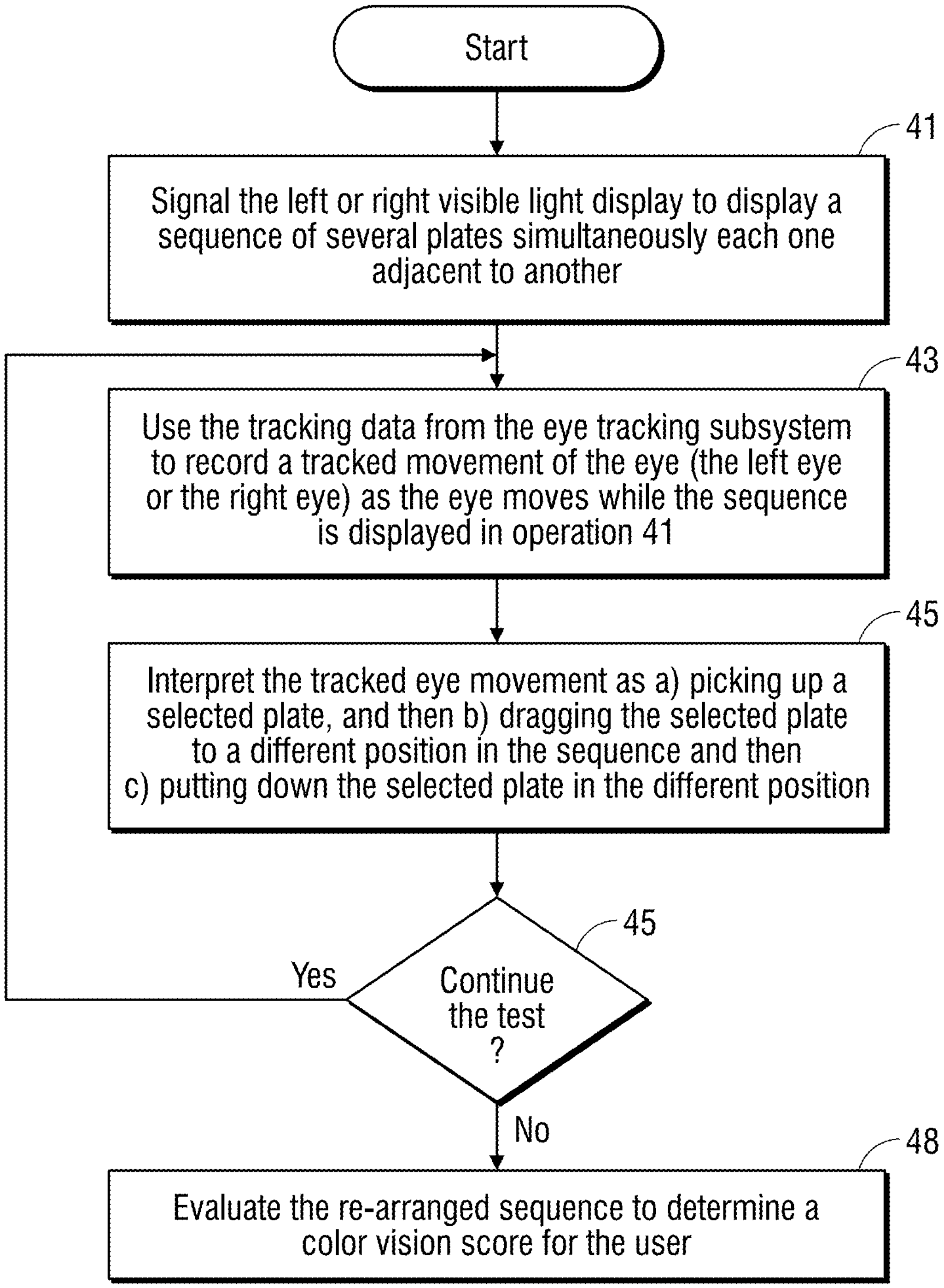
FIG. 4 is a flow diagram of an example method for an arrangement-type color vision test.

Turning now to FIG. 4, this is a flow diagram of an example method for an arrangement-type color vision test. The test is performed by a processor in the VR-based headset system of FIG. 1. Once the user has fitted the VR headset 1 over their eyes, and may be instructed to look for a visual stimulus, the processor is configured, in operation 41, to signal the left or right visible light display to display a sequence of several plates, e.g., all shaped like disks or squares, simultaneously each one adjacent to another. Note here that the sequence need not form a straight line as it may be curved, and it also need not be an open sequence as it may instead form a closed loop.

The user is now instructed to re-arrange the plates in the sequence, in correct color order. For example, the user is instructed to locate the plate that they feel is closest in color to a starting plate. The starting plate may be highlighted, or it may be at one end of the sequence and may remain fixed during the test. Once the user has located their first selected plate, the first selected plate is to be "picked up" and then "put down" adjacent to the starting plate. Next, the user will choose a second plate, which is closest in color to the first plate, and then the second plate is picked up and moved to adjacent the first plate where it is put down. This process is to be repeated until the user or the processor decides that the sequence re-ordering is complete, e.g., all remaining plates except for the first plate have been picked up at least once. There are variations to this process, e.g., where the user is allowed to make all decisions on which plate to select next, or where the user can return to re-arrange a previously arranged plate.

To enable a hands-free version of the plate arranging process, the processor is configured, in operation 43, to use the tracking data from the eye tracking subsystem 8 to record a tracked movement of the eye (the left eye or the right eye) as the eye moves while the sequence is displayed in operation 41. The processor then interprets the tracked eye movement as a) picking up a selected plate, and then b) dragging the selected plate to a different position in the sequence and then c) putting down the selected plate in the different position (operation 45.) For example, the tracked movement of the eye may be interpreted as the user staring at the plate (rather than glancing at it), which in turn is interpreted as picking up or selecting the plate or putting down the plate (depending on the surrounding context of the tracked movement of the eye.) Alternatively, or in addition to interpreting the tracked eye movement, the processor in operation 45 detects a first blink of the eye, when the gaze is on the plate, as picking up the plate, and then detects a second blink of the eye as putting down the selected plate. The position where the plate is put down is indicated by the location at which the user's eye is gazing at the moment of the detected blink. Operation 45 may be repeated several times to result in a re-arranged sequence of the plates, when a decision is made by the processor that the test has ended (operation 47.) And in operation 48, the processor evaluates the re-arranged sequence to determine a color vision score for the user, for example according to any one of several available techniques, e.g., Farnsworth D-15.

Figure 5:
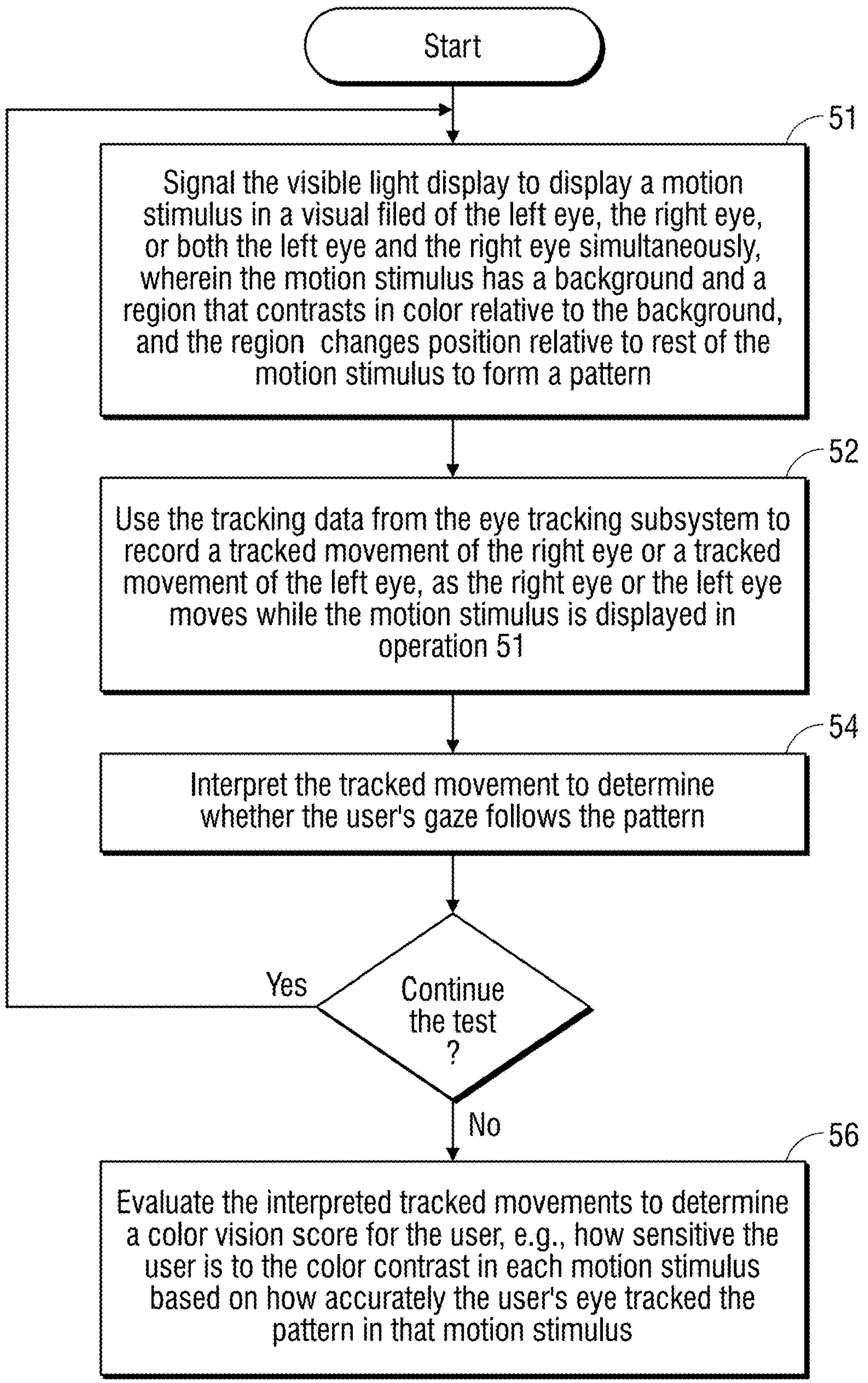
FIG. 5 is a flow diagram of an example method for color vision testing using a motion stimulus.

Turning now to FIG. 5, this is a flow diagram of a method for color vision testing in which a motion stimulus is displayed to the user. The method may be implemented by a processor of a computer system having a visible light display and a non-visible light-based eye tracking subsystem. The display may be a tabletop display screen and the eye tracking subsystem is mountable to the tabletop display screen such that it can monitor the user's eyes while the user is looking at the display screen. Alternatively, the display and the eye tracking subsystem are attachable to or are integrated within a VR headset that user fits over their eyes, such as the VR headset 1 described above in connection with FIG. 1. The method may begin in operation 51 where the processor signals the visible light display to display a motion stimulus in a visual field of the left eye, the right eye, or both the left eye and the right eye simultaneously. The motion stimulus has a background and a region that contrasts in color relative to the background, e.g., a PIP. A 'color pair' in any PIP is the object or figure hue and the background hue, meant to test for a particular type of color blindness. The region changes position or moves relative to rest of the motion stimulus, to form a pattern. The region may also be referred to below as a figure or object that is hidden within, and moves, in the PIP. The expectation here is that a different object or figure (with a different motion path) would be apparent to people with distinct types or degrees of color-blindness. For example, in the case of presenting two objects, it is expected that in most instances a user only observes one of the two objects, whichever object they see with greater contrast.

In operation 52, the processor uses the tracking data from the eye tracking subsystem 8 to record a tracked movement of the right eye or a tracked movement of the left eye, as the right eye or the left eye moves while the motion stimulus is displayed in operation 51. It also interprets the tracked movement to determine whether the user's gaze follows the pattern (operation 54.) These operations 51-54 are repeated several times each time with a different motion stimulus, and then in operation 56 the processor evaluates the interpreted tracked movements to determine a color vision score for the user, e.g., how sensitive the user is to the color contrast in each motion stimulus based on how accurately the user's eye tracked the pattern in that motion stimulus.

In one aspect, there may be a single region in the entire visual field of the user that changes position slowly over time. In another aspect, there are multiple such regions appearing simultaneously at various locations in the user's visual field, e.g., where each region is a figure that is effectively hidden within a respective, PIP (hidden only from individuals having impaired color vision.) There may be several such PIPs that are uncorrelated and are being displayed simultaneously. In such a scenario, the user may be instructed to look for the hidden figure (within its respective PIP or plate) that appears with highest contrast from its background. There may be several of such plates at similar levels of color contrast, and if the user's gaze is interpreted as having stared at all of them (sequentially of course) then the measurement of color sensitivity obtained from such a stimulus is more likely to be accurate (or has a greater confidence score.) One or more of these regions or plates may disappear and then reappear elsewhere, as part of the motion stimulus, and the user's gaze upon them is tracked and interpreted to determine the color vision score.

Figure 6:
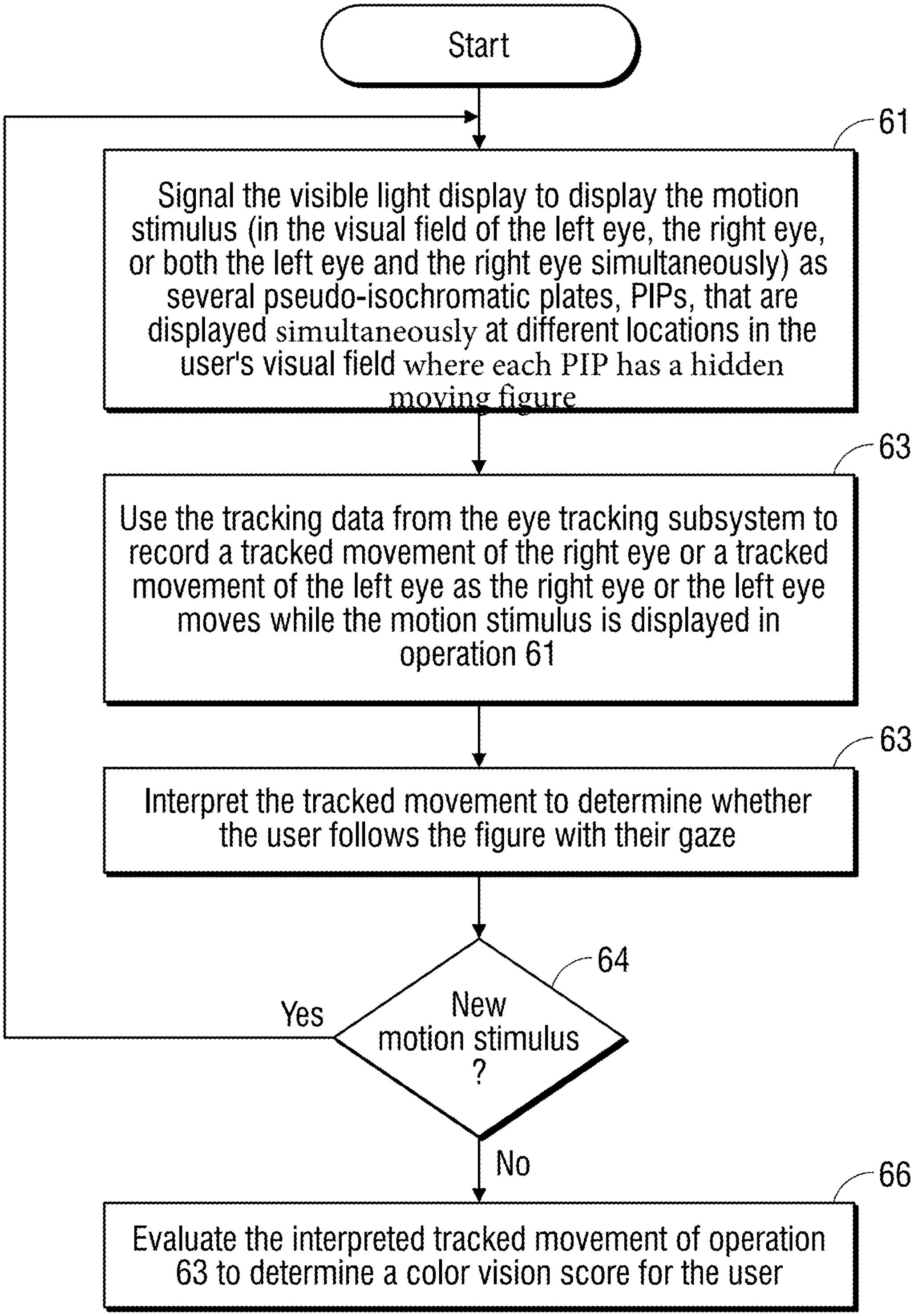
FIG. 6 is a flow diagram of yet another method for color vision testing using a motion stimulus.

In another aspect, where there are multiple such regions appearing simultaneously at various locations in the user's visual field, all of the regions are changing color or intensity over time, and a blob containing one more of such regions will change according to a target or desired color scheme, relative to the remaining background. The blob moves around the visual field of the user, and the user is instructed to find and then follow the blob that is in a color different than the background. FIG. 6 is a flow diagram of such a method for color vision testing in which a motion stimulus is displayed to the user. The method may be performed by a processor of a color vision system such as one described above, having a non-visible light-based eye tracking subsystem that produces tracking data for a left eye and for a right eye of a user, and a visible light display to display the motion stimulus in a visual field of the left eye, the right eye, or both the left eye and the right eye simultaneously. In this method, the processor is configured to signal the visible light display to display the motion stimulus (in the visual field of the left eye, the right eye, or both the left eye and the right eye simultaneously) as several PIPs where each PIP contains a hidden figure that moves within the respective PIP (operation 61.) A figure is hidden in the PIP in the sense that an individual with impaired color vision will be unable to see or stare at it. In operation 63, the processor uses the tracking data from the eye tracking subsystem to record a tracked movement of the right eye or a tracked movement of the left eye as the right eye or the left eye moves while the motion stimulus is displayed in operation 61, and interprets the tracked movement to determine whether the user follows the figure with their gaze. The operations 61-63 i)-iii) may be repeated at least once, each time with a different motion stimulus (operation 64.) The processor then evaluates the interpreted tracked movements of operation 63 to determine a color vision score for the user (operation 66.)

In one version of the method described above in FIG. 5 or in FIG. 6, each of the PIPs or each instance of the PIP has a background of bubbles and the figure in the PIP is a blob of one or more bubbles in foreground. Also, the blob changes not only in color hue but also monochromatic intensity or color saturation, from one PIP to a next PIP. The background pattern of bubbles from one plate to the next may be kept spatially consistent within the user's field of view, to provide visual continuity which may make the color vision test more comfortable for the user. In another aspect, color intensity or chroma of a majority of all bubbles that make up each PIP is dithered from one PIP to the next PIP. This may advantageously disrupt hyperacuity artifacts. Such artifacts could allow the user to see a change in pixel value in an isolated area that is actually below their general threshold of color perception. The intensity or color trajectory of a bubble over multiple plates may be made smooth to give the impression of a smoothly flowing bubble, rather than a noisy temporal static.

The hidden figure may move smoothly. This continuity enables the user to experience a stress free and intuitive smooth pursuit task, rather than searching the field for the figure in a random area. This also allows the analysis of the eye tracking data to be much simpler because there will be fewer uncorrelated searching eye movements in the eyes of normally sighted individuals.

The contrast in a first color pair may be compared to observed contrast in a second color pair or monochromatic intensity contrast. Testing both color contrast and monochromatic intensity contrast in a similar testing format aids to describe the two on a common scale. In the Ishihara test, a region composed of multiple bubbles have a different hue range than a neighboring background. In a similar test for monochromatic contrast sensitivity, a region composed of multiple bubbles has a different value range than a neighboring background. Alternatively, the two patterns may be tested against each other in a forced choice test: For example, a mean difference in color bubble pattern moves in a different direction to a mean difference in value pattern and contrast in each can be adjusted for threshold. For example, a ball shape pattern encoded in hue limits might move in clockwise direction while another ball shaped pattern encoded in the value limits might move in a counterclockwise direction. User perception would be observable by asking user to follow the object they see moving, and observing the gaze with an eye tracker as a smooth pursuit task. Depending on the pattern traced by user's gaze, at various levels and types of color vs amplitude contrast, can determine color perception threshold.

In one aspect, the motion stimulus has small bubbles of quasi random size, color, and intensity, superimposed with trends in color and intensity that will be seen as a different figure depending on the relative color and intensity contrast sensitivity of the user. Multiple motion patterns are occasionally superimposed, which can track together for a brief period and then diverge from each other. This forced choice at path divergence eliminates favoring continued pursuit of a barely observable object while a higher contrast object might be present elsewhere in the field that does not currently have the user's attention. A quasi random motion path or display rate prevents false measures of contrast perception that might be achieved by continuing along a path previously traced at higher contrast along a fixed pattern. Superimposed temporal noise in size, color, and intensity of each bubble can be added to mask hyperacuity effects that might not represent the true color contrast perception of the user.

In another version of the methods described above in FIG. 5 or FIG. 6, each of the PIPs has a background of bubbles and the figure is a blob of one or more bubbles in foreground, wherein in some of the PIPs the blob has a different hue range than the background, and in some others of the PIPs the blob has a different brightness or value range than the background.

In yet another version of the method of FIG. 5 or FIG. 6, each of the PIPs has a background of bubbles and the figure is made of at least a first blob of one or more bubbles and a second blob of one or more bubbles. The first blob has a different hue range than the background and the second blob have a different brightness or value range than the background, and the first blob is seen to move in a different direction than the second blob.

In still another version of the method in FIG. 5 or FIG. 6, the processor is further configured to signal the visible light display to display a horizontally moving set of vertical contrasted stripes, simultaneously with the motion stimulus in operation 61. The processor in operation 63 also evaluates the tracked movement of the user's eye to determine whether the user is gaming the system. In this connection, consider that a broad background in the user's visual field that appears to be moving horizontally may not cause the user to consciously follow a particular portion of the motion stimulus pattern, however it may be impossible for the user's eyes not to zag to attempt to stabilize the pattern. Such a pattern may be especially useful to eliminate the possibility of gaming the exam. In this case, presenting a horizontally moving set of vertical contrasted stripes may be useful on its own or in combination with other stimuli described here. In this case it may also be useful to reduce or eliminate the high spatial frequency contrast provided by the bubbles, which might allow the user to anchor their eyesight on a particular bubble. On the other hand, such an artificial anchoring at a single point should be quite easily detectable and might be an especially useful "tell" of a person attempting to game the system to achieve a negative result.

A similar testing strategy may be used to test low spatial frequency intensity contrast.

In another aspect of the disclosure here, the color vision test has a dynamic number of iterations, rather than a predetermined or fixed number. For instance, referring to the example of FIG. 2A where each iteration is a single pass through the operations 13-18, in a dynamic version of the test a different number of such iterations may be performed when the processor decides that the test is complete or has ended. Each time the test is administered, for example on a different person, or on the same person but at various times, the processor may compute a confidence score that it may update after each iteration. The confidence score may refer to the level of certainty or reliability associated with the seen/not seen responses from the user. The test may start with the processor accessing a prior assumption of the user's color contrast sensitivity (e.g., a probability distribution of population normal or a flat distribution of all contrast sensitivities.) The processor then asks questions of the user in terms of each presented PIP stimulus that would usefully segment the current estimation with a seen or not seen response. There is a likelihood function associated with each answer to a particular question, which the processor can access; for example, if a user answers a particular question correctly then there is a probability distribution of their contrast sensitivity (that the processor can access), and a different probability distribution if they answer incorrectly, independent of any prior knowledge. After each presentation and response, the processor calculates the updated probability distribution of the user's color contrast sensitivity by multiplying the pre-question (previous) probability distribution function by the answer likelihood function; the processor ceases presenting stimuli when the patient's sensitivity is known to within a preset limit of confidence, for example when the standard deviation of the probability distribution function declines below a fixed value. Alternatively, the processor could present a monotonic staircase of contrast sensitivity questions. In a staircase of descending contrast, the stop criterium is met when the user fails a set of number of questions. The user's color contrast sensitivity is estimated at a level between where they could reliably pass the question and would reliably fail the question, e.g., an estimate of where the user would pass the question 50% of the time.

In one version of the color vision systems described above, the processor may be external to the VR headset 1, and the VR headset 1 has a wired or wireless communications network interface through which the tracking data from the eye tracking subsystem 8 is sent to the processor. An alternative to such a system is where the processor is integrated in a housing of the VR headset 1, or where the processor implemented operations of the flow diagrams described above are distributed amongst different processors in the VR headset 1 and in the external computing device 9.

In one aspect, the eye tracking subsystem 8 is an infrared pupil tracking subsystem that produces images of pupils of the left eye and the right eye. The eye tracking subsystem 8 in that case may image the entirety of the left eye and the entirety of the right eye, and wherein the processor determines gaze angles of the left eye and the right eye based on: knowledge of distance between the right visible light display and the left visible light display; distance between the right eye and the right visible display; and location of a left pupil within the left eye and a right pupil within the right eye, or interpupillary distance.

In another aspect, the VR headset 1 has one or more light sensors that can be used to detect levels of light inside the left compartment and the right compartment, and the processor is configured to record the levels of light for the left compartment and the right compartment representing external light contribution while the user is wearing the VR headset 1. To avoid affecting the results of the test in an unrepeatable manner, and thereby make the test more reliable, the processor controls a parameter of the display (the left display 3 or the right display 4) to ensure that lighting in the compartment (the left compartment 5 or the right compartment 6, respectively), or chromaticity of the display, is consistent each time the color vision tested is conducted. The parameter is dependent on a color palette of the display and the nature of the lighting in the compartment.

The following statements of invention may be made, based on the description above:

15. A color vision testing system comprising:
  - a non-visible light-based eye tracking subsystem that produces tracking data for a left eye or for a right eye of a user; and
  - a processor configured to
    - i) signal a visible light display to display a motion stimulus in a visual filed of the left eye, the right eye, or both the left eye and the right eye simultaneously, wherein the motion stimulus comprises a background and a region that contrasts in color relative to the background, wherein the region changes position relative to rest of the motion stimulus to form a pattern;
    - ii) use the tracking data from the eye tracking subsystem to record a tracked movement of the right eye or a tracked movement of the left eye as the right eye or the left eye moves while the motion stimulus is displayed in i),
    - iii) interpret the tracked movement to determine whether the user follows the pattern with their gaze, and
    - iv) repeat i)-iii) a plurality of times each time with a different motion stimulus.

16. The system of statement 15 wherein the processor is further configured to evaluate iii)-iv) to determine a color vision score for the user.

17. The system of any one of statements 15-16 wherein the display is a tabletop display screen and the eye tracking subsystem is mountable to the tabletop display screen.

18. The system of any one of statements 15-16 wherein the display is a display screen integrated in a housing of a tablet computer, and the eye tracking subsystem is integrated in the housing of the tablet computer.

19. The system of any one of statements 15-16 wherein the display and the eye tracking subsystem are attached to or form part of a virtual reality headset.

20. A color vision testing system comprising:
  - a non-visible light-based eye tracking subsystem that produces tracking data for a left eye or for a right eye of a user; and a processor configured to i) signal a visible light display to display a motion stimulus in a visual field of the left eye, the right eye, or both the left eye and the right eye simultaneously, wherein the motion stimulus comprises a pseudo-isochromatic plate, PIP, and wherein a figure that moves is hidden in the PIP, ii) use the tracking data from the eye tracking subsystem to record a tracked movement of the right eye or a tracked movement of the left eye as the right eye or the left eye moves while the motion stimulus is displayed in i), iii) interpret the tracked movement to determine whether the user follows the figure in the PIP with their gaze, iv) repeat i)-iii) at least once each time with a different motion stimulus, and v) evaluate iii)-iv) to determine a color vision score for the user.

21. The system of statement 20 wherein each of the PIPs comprises a background of bubbles and the figure is a blob of one or more bubbles in foreground, wherein the blob changes in color hue and monochromatic intensity or color saturation, from one PIP to a next PIP.

22. The system of statement 21 wherein color intensity or chroma of a majority of all bubbles that make up each PIP is dithered from one PIP to the next PIP.

23. The system of statement 20 wherein each of the PIPs comprises a background of bubbles and the figure is a blob of one or more bubbles in foreground, and wherein in some of the PIPs the blob has a different hue range than the background, and in some others of the PIPs the blob has a different brightness or value range than the background.

24. The system of statement 20 wherein each of the PIPs comprises a background of bubbles and the figure comprises a first blob of one or more bubbles and a second blob of one or more bubbles, the first blob has a different hue range than the background, the second blob has a different brightness or value range than the background, and the first blob is seen to move in a different direction than the second blob.

25. The system of statement 20 wherein the processor is further configured to signal the visible light display to display a horizontally moving set of a vertical contrasted stripes simultaneously with the motion stimulus in i) and evaluate the tracked movement to determine whether the user is gaming the system.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A system comprising:

a VR headset comprising a left visible light display, a left compartment to fit over a left eye of a user, a right visible light display, a right compartment to fit over a right eye of the user, wherein the left and right compartments are configured so that when the headset has been fitted over the user's eyes a) the user cannot see the right display using only their left eye and b) the user cannot see the left display using only their right eye, and a non-visible light-based eye tracking subsystem that produces tracking data for the left eye and for the right eye, wherein the left and right compartments are opaque and configured to block ambient light originating external to the left and right compartments to create a light-controlled environment around the user's eyes; and a processor configured to, when the headset has been fitted over the user's eyes:

i) signal the left or right visible light display to display i) a pseudo isochromatic plate, PIP, for a color vision test, and simultaneously ii) a plurality of user selectable figures;

ii) use the tracking data from the eye tracking subsystem to record a tracked position of the right eye or a tracked position of the left eye as the right eye or the left eye moves while the PIP is being shown in i);

iii) interpret the tracked position of the right eye or the left eye to determine a user selectable figure that has been selected by the user from amongst the plurality of user selectable figures; and iv) record an indication as to whether the user has seen a stimulus figure in the PIP, based on a comparison between the stimulus figure and user selectable figure.

2. The system of claim 1 wherein the processor controls a parameter of the left or right display to ensure that lighting in the left or right compartment, or chromaticity of the left or right display, do not affect results of the test in an unrepeatable manner.

3. The system of claim 1 wherein the processor performs i)-iv) a plurality of times, wherein each time the PIP contains a different stimulus figure, to record a plurality of indications as to whether the user has seen the stimulus figure.

4. The system of claim 1 wherein the processor is configured to, when the headset has been fitted over the user's eyes, i) signal the left or right visible light display to display a second PIP for the color vision test, the second PIP contains a second stimulus figure;

ii) use the tracking data from the eye tracking subsystem to record a tracked movement of the right eye or a tracked movement of the left eye as the right eye or the left eye moves while the second PIP is being shown;

iii) interpret the tracked movement of the right eye or the left eye; and iv) record an indication as to whether the user has seen the second stimulus figure based on interpreting the tracked movement as showing a hesitancy by the user.

5. The system of claim 4 wherein the processor is configured to quantify the hesitancy and use the hesitancy to provide more information than just binary correct or incorrect.

6. The system of claim 1 wherein the processor completes the test on the user without receiving manual input from the user on whether the user has seen the stimulus figure.

7. The system of claim 6 wherein the processor is further configured to interpret tracking data of the eye tracking subsystem to detect a blink by the user while the PIP plate is being displayed in i) and determine the user selected figure based on the detected blink.

8. The system of claim 1 wherein the processor performs i)-iv) a plurality of times, wherein each time the display of the PIP in i) alternates between the left visible light display and the right visible light display, and in iv) the indication as to whether the user has seen the stimulus figure in the PIP refers to only the left eye or only the right eye.

9. The system of claim 1 wherein the processor is external to the VR headset, and the VR headset comprises a wired or wireless communications network interface through which the tracking data from the eye tracking subsystem is sent to the processor.

10. The system of claim 1 wherein the eye tracking subsystem is an infrared pupil tracking subsystem that produces images of pupils of the left eye and the right eye.

11. The system of claim 1 wherein the eye tracking subsystem images the entirety of the left eye and the entirety of the right eye, and wherein the processor determines gaze angles of the left eye and the right eye based on:

knowledge of distance between the right visible light display and the left visible light display;

distance between the right eye and the right visible display; and location of a left pupil within the left eye and a right pupil within the right eye, or interpupillary distance.

12. The system of claim 1 wherein the VR headset comprises one or more light sensors that can be used to detect levels of light inside the left compartment and the right compartment, and the processor is configured to record the levels of light for the left compartment and the right compartment representing external light contribution while the VR headset is fitted to the user.

13. A system comprising:

a left visible light display;

a left compartment to fit over a left eye of a user;

a right visible light display;

a right compartment to fit over a right eye of the user, wherein the left and right compartments are configured so that when the system-has been fitted over the user's eyes i) the user cannot see the right display using only their left eye and ii) the user cannot see the left display using only their right eye, wherein the left and right compartments are opaque and configured to block ambient light originating external to the left and right compartments to create a light-controlled environment around the user's eyes;

a non-visible light-based eye tracking subsystem that produces tracking data for the left eye and for the right eye; and a processor configured to, when the system has been fitted over the user's eyes:

i) signal the left or right visible light display to display a sequence of a plurality of plates, for an arrangement-type color vision test;

ii) use the tracking data from the eye tracking subsystem to record a tracked movement of the right eye or a tracked movement of the left eye as the right eye or the left eye moves while the sequence is displayed in i);

iii) interpret the tracked movement or detecting a blink of the right eye or the left eye as a) picking up a selected plate, of the plurality of plates, and then b) dragging the selected plate to a different position in the sequence and then c) putting down the selected plate in the different position;

iv) repeat iii) a plurality of times to result in a re-arranged sequence of the plurality of plates; and v) evaluate the re-arranged sequence to determine a color vision score for the user.

14. The system of claim 13 wherein for a) and for c), the processor interprets the tracked movement of the right eye or the left eye as the user staring at the selected plate.

15. The system of claim 13, further comprising a light sensor positioned to measure a light level inside one of the left compartment or the right compartment, wherein the processor is further configured to, when the system has been fitted over the user's eyes, to:

detect an external light contribution within the one of the left compartment or the right compartment based on measuring the light level.

16. The system of claim 15, wherein the processor is further configured to, when the system has been fitted over the user's eyes, to:

controlling a parameter of at least one of the left display or the right display to maintain a consistent lighting level or a consistent chromaticity across multiple color vision tests for the user, wherein the controlling is based upon one or more measurements acquired with the light sensor.

* * * * *